United States Patent [19]
Phillips

[11] Patent Number: 5,376,141
[45] Date of Patent: Dec. 27, 1994

[54] LOW-PROFILE SYMES FOOT PROSTHESIS

[76] Inventor: Van L. Phillips, 5499 Avenida Maravillas, Rancho Santa Fe, Calif. 92067

[21] Appl. No.: 171,257

[22] Filed: Dec. 21, 1993

Related U.S. Application Data

[63] Continuation of Ser. No. 87,472, Jul. 6, 1993, abandoned, which is a continuation of Ser. No. 926,548, Aug. 5, 1992, abandoned, which is a continuation of Ser. No. 755,680, Sep. 6, 1991, abandoned, which is a continuation-in-part of Ser. No. 585,920, Sep. 21, 1990, abandoned.

[51] Int. Cl.⁵ .................... A61F 2/66; A61F 2/62
[52] U.S. Cl. ............................ 623/55; 623/38; 623/52
[58] Field of Search ................... 623/38, 47–56

[56] References Cited

U.S. PATENT DOCUMENTS

| | | | |
|---|---|---|---|
| 277,562 | 5/1883 | Furrer | 623/49 X |
| 2,440,075 | 4/1948 | Campbell | 623/50 |
| 4,177,525 | 12/1979 | Arbogast et al. | |
| 4,328,594 | 5/1982 | Campbell et al. | |
| 4,636,220 | 1/1987 | Ziegelmeyer | 623/53 |
| 4,721,510 | 1/1988 | Cooper et al. | 623/55 |
| 4,822,363 | 4/1989 | Phillips | 623/27 |
| 4,865,612 | 9/1989 | Arbogast et al. | |
| 4,892,553 | 1/1990 | Prahl | |
| 4,994,086 | 2/1991 | Edwards | 623/26 |
| 5,037,444 | 8/1991 | Phillips | 623/55 |

FOREIGN PATENT DOCUMENTS

| | | | |
|---|---|---|---|
| 0120445 | 11/1918 | United Kingdom | 623/53 |
| 1432481 | 4/1976 | United Kingdom | 623/47 |
| 0397204 | 9/1973 | U.S.S.R. | 623/53 |
| 1465045 | 3/1989 | U.S.S.R. | 623/53 |

*Primary Examiner*—David H. Willse
*Attorney, Agent, or Firm*—Knobbe, Martens, Olson & Bear

[57] ABSTRACT

A prosthetic foot is characterized by a low-profile, elongated forefoot portion incorporating an attachment section, an arch section and a toe section, said forefoot portion being configured so that the foot may be worn by Symes-type amputees. The foot further preferably includes a heel portion secured to the forefoot portion. A preferably demountable connection of the heel portion to the forefoot portion permits interchangeability of those components to match the weight, stride and activity schedule of the wearer utilizing the prosthetic foot. Adjustment means is provided to permit adjustment and alignment of the foot with respect to the wearer's stump.

16 Claims, 4 Drawing Sheets

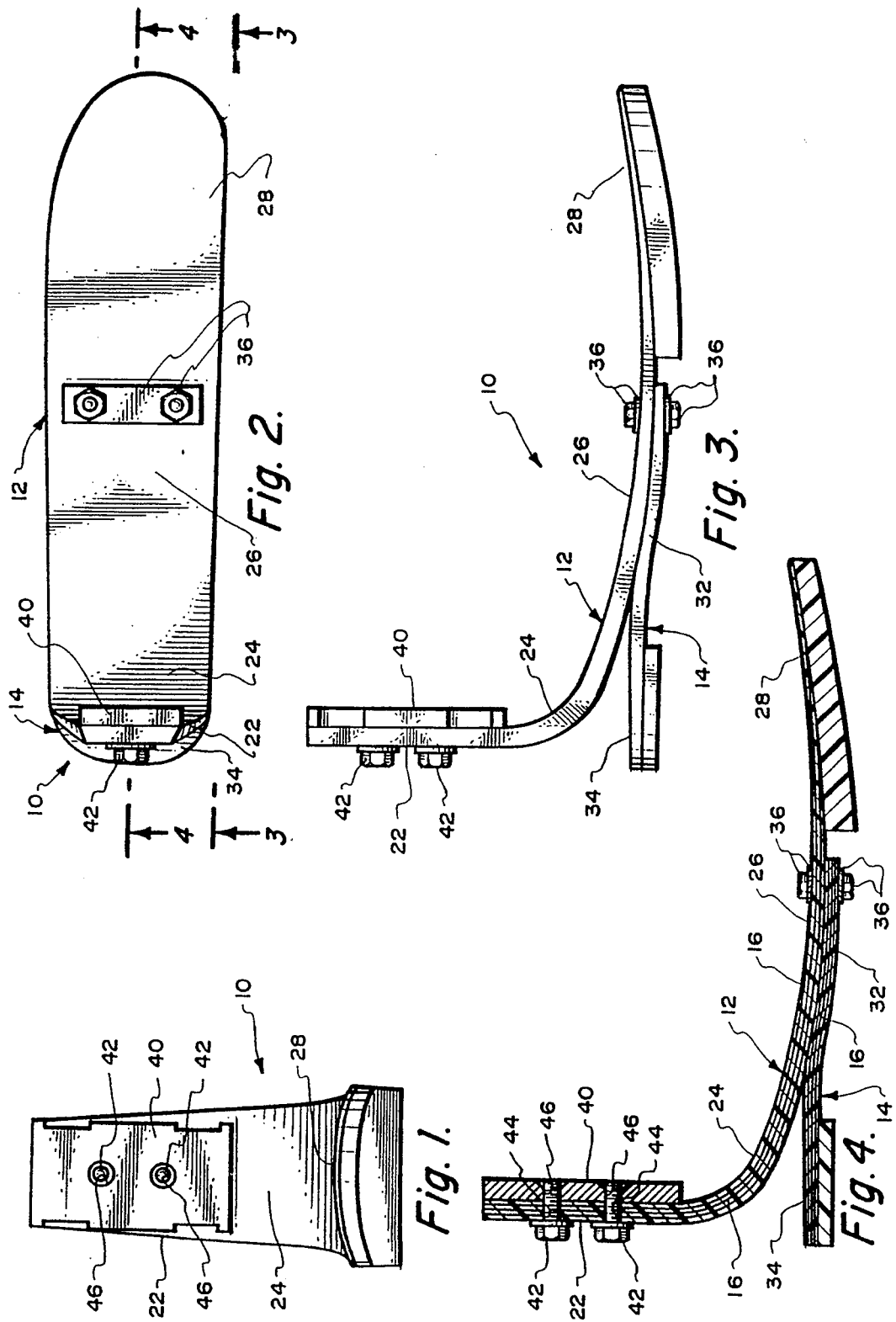

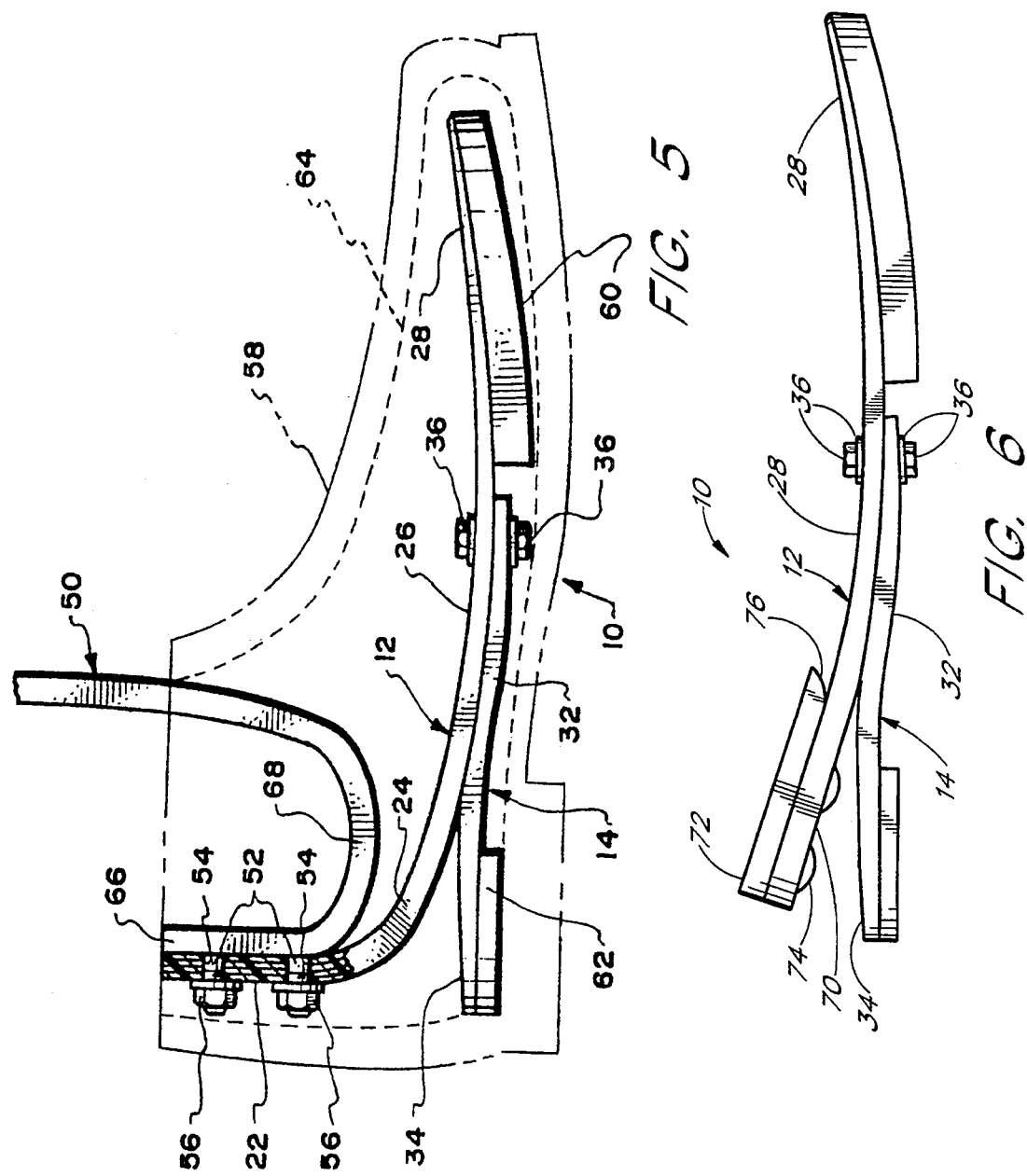

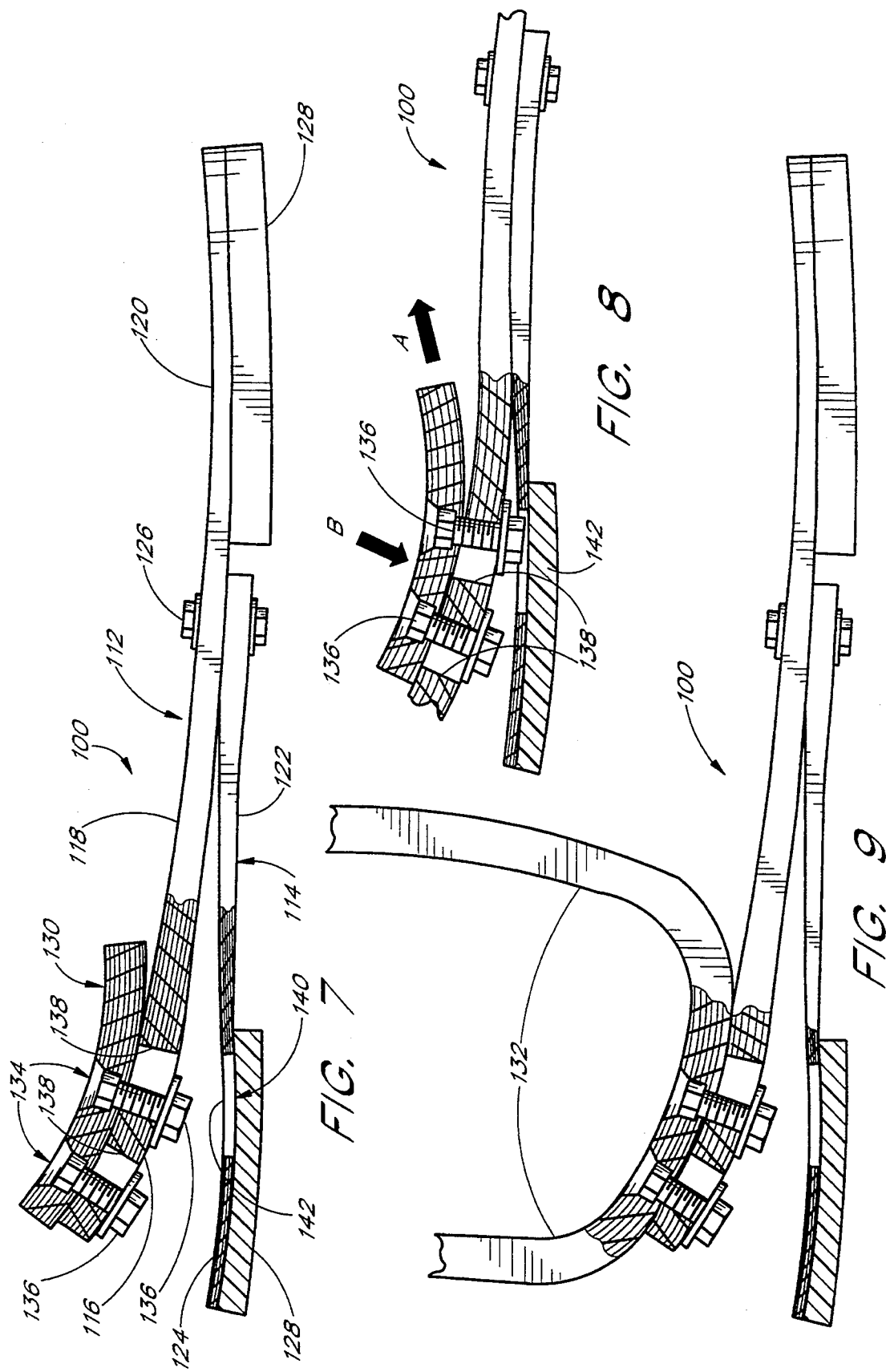

LOW-PROFILE SYMES FOOT PROSTHESIS

This application is a continuation of application Ser. No. 08/087,472, filed Jul. 6, 1993, now abandoned, which is a continuation application of Ser. No. 07/926,548, filed Aug. 5, 1992, now abandoned, which is a continuation application of Ser. No. 755,680, filed Sep. 6, 1991. now abandoned, which is a continuation-in-part of Ser. No. 585,920, filed Sep. 21, 1990, now abandoned.

BACKGROUND OF THE INVENTION

This invention relates to foot prostheses in general, and specifically to a prosthetic foot adapted for use by persons who have undergone what is known in the art as a Symes amputation. This amputation severs the foot from the leg near the ankle region. Because the Symes patient's calf and shin functions as the patient's stump for prosthetic purposes, any prosthetic device utilized by the patient must either be relatively compact so as to be attachable below the point of amputation, or must be configured to accommodate the patient's shin and calf while attached thereto or higher up on the wearer's leg.

Prior art prostheses available to Symes patients typically include an artificial foot bonded or bolted onto the bottom end of a socket worn on the patient's stump. Examples of prior art Symes-type prostheses include U.S. Pat. No. 3,874,004 to May, which teaches an artificial ankle joint which can pivot in simulation of a natural ankle, and U.S. Pat. No. 4,225,982 to Cochrane, which teaches an elongated socket secured to a rubber-filled cavity of a slipper member.

Other prosthetic foot devices include U.S. Pat. No. 3,335,428 to Gajdos, which attempts to duplicate the skeletal and skin structure of a natural human foot, U.S. Pat. No. 2,075,583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

These and other prosthetic foot devices, however, have significant deficiencies; for example, the May '004 and the Cochrane '982 patents achieve relatively focused and limited stress response because of their structure and reliance on hardened rubber members for flexure. Moreover, the component parts of the prostheses are too heavy and too rigid, as in Lange, or are too massive and monolithic, as in Poggi, to respond properly to the nuances of stress-response gradients characteristic of the human foot.

Certain of these performance deficiencies are overcome in U.S. Pat. No. 4,547,913 for my invention relating to a "Composite Prosthetic Foot and Leg", U.S. Pat. No. 4,822,363 for my invention relating to a "Modular Composite Prosthetic Foot and Leg", and U.S. Pat. No. 5,037,444 for my invention relating to a "Prosthetic Foot". Also, my pending application Ser. No. 07/337,374 discloses a prosthetic foot device with similar preferred materials and methods of manufacture, and with corresponding benefits therefrom.

Each of my aforementioned inventions is characterized by lightweight, elongated structures incorporating polymer impregnation of superimposed reinforcing laminae or fibers maintained in the desired configuration. Such configurations and constructions provide the desirable characteristics of strength and flexibility in the prosthetic member, and achieve a simulation of the performance of natural feet which had previously not been attainable. Such prostheses may be provided in modular assemblies, whereby the particular performance characteristics of a given prosthesis may be adapted and readily adjusted to meet the needs and activity level of the individual patient.

None of my prior inventions, however, is readily utilized by Symes amputees, because of the various constraints set forth above. Among other things, my prior prosthetic inventions are not configured to accommodate affixation to a Symes-type stump, in that the prostheses are not compact enough to be attachable below the point of amputation, nor are they configured to accommodate the patient's shin and calf while attached thereto or higher up on the wearer's leg.

OBJECTS AND ADVANTAGES OF THE INVENTION

It is, therefore, an object of my invention to provide a low-profile prosthetic foot suitable for use by Symes amputees, which foot incorporates the desirable lightweight, flexible, energy-absorbing and energy-storing performance of certain of my prior inventions.

It is a further object of my invention to provide a prosthetic foot of the aforementioned character which is of modular configuration, resulting in ready assembly and adjustability thereof. The foot of my invention preferably includes forefoot and heel portions that can be readily exchanged with correspondingly-constructed forefoot and heel portions to provide size adjustment or different spring rates to suit the size of foot of the amputee or the stride, height, weight, and activity level of the amputee. Therefore, a range of combinations of spring rate and size can be provided to the amputee, achieving a natural stride and resilience of gait, which has not been fully obtainable by prior art prosthetic devices.

In addition to bringing important benefits to Symes amputees, my invention may be utilized in connection with pylons by being operatively attached to the lower end thereof, and would thereby be useful to non-Symes amputees in certain applications.

The preferred embodiment of the invention is characterized by its low profile, which permits utilization by amputees having very low Symes amputations. Moreover, my invention provides means for adjustability for desired and necessary planarflexion and dorsiflexion of the foot.

It is a further object of my invention to provide a low-profile prosthetic foot which is characterized by a forefoot portion incorporating an attachment section and an arch section and a toe section extending forwardly therefrom, said attachment section being configured to be operatively positioned, retained and utilized below a wearer's stump; and a heel portion having an attachment section secured to said forefoot portion and a heel section extending rearwardly therefrom. In a preferred embodiment, the heel portion is demountably attached to the forefoot portion to permit heel portions having different spring rates to be secured to said forefoot portion of said foot.

An additional object of my invention is to provide a lower leg prosthesis having an attachment means for attaching the prosthesis below a wearer's stump, in combination with an elongated, substantially flat forefoot portion, said forefoot portion including an attachment section for operative alignment and retention of the prosthesis under the wearer's stump, and an arch section and a toe section extending forwardly therefrom.

It is a further object of my invention to provide a prosthetic foot of the aforesaid character which is fabricated from superimposed laminates maintained in operative relationship by an encapsulating polymer and susceptible to bending stress determined by the dimensions of the laminates, or from chopped fiber maintained in operative relationship by an encapsulating polymer and susceptible to bending stress determined by the cross-section of the respective heel and/or forefoot portions.

Yet another object of my invention is the provision of a prosthetic foot of the aforementioned character which may be utilized with one or more auxiliary support members to permit fine-tuning of the performance characteristics of the foot.

Another object of my invention is the provision of a prosthetic foot of the aforementioned character having a forefoot portion of unitary structure which is continuous, integrally and simultaneously formed to provide spring stress generated energy storage, whereby the subjection of said toe section to bending moments will cause uniform transmission of spring stress through said arch and said toe sections to said attachment section.

The polymers utilized to encapsulate the fibrous laminae or chopped fiber are characterized by elasticity and flexibility so that the foot prosthesis deflects proportionally to the engagement of said prosthetic foot with an adjacent surface, causing the resultant energy to be stored and subsequently released when the gait of the amputee incorporating thrust and lift components results in the utilization of the stored energy and a consequent reduction of the energy expended by the amputee.

In order to impart a cosmetic aspect to the prosthetic foot, after proper fitting of the foot to insure that it is properly balanced and of appropriate size, the prosthesis may be encapsulated in a suitably shaped cosmetic shroud. The shroud must be sufficiently flexible so as not to inhibit the free movement and flexure of the foot, but, because of the inherently resilient and stress-absorbing characteristics of said foot, little dependence is needed upon the ancillary cushioning action of the shroud.

consequently, the foot of my invention is characterized by extreme light weight, instantaneous response to imposed loads and correspondingly instantaneous delivery of stored energy when the gait of the wearer indicates that such stored energy is to be released. The wearer of the foot may engage in a wide variety of activities which were precluded in the past, or in activities in which the wearer's enjoyment was limited, because of the structural limitations and corresponding performance of prior art prostheses. Running, jumping and other activities are sustained by the foot and it may be utilized in substantially the same manner as the normal foot of the wearer.

Another object of my invention is to provide a prosthesis of the aforementioned character that may be completely or substantially disposed within the patient's shoe, thus providing an optimum cosmetic appearance.

An additional object of my invention is the provision of a prosthetic foot of the aforementioned character in which the aforedescribed forefoot and heel portions may be manufactured by various expedients, including injection molding and/or the use of thermoplastic materials and processes, or any of a range of combinations thereof.

Other objects and advantages of the invention will be apparent from the following specification and the accompanying drawings, which are for the purpose of illustration only.

BRIEF DESCRIPTION OF THE DRAWINGS

FIG. 1 is a front elevation view of an alternative embodiment of a prosthesis constructed in accordance with the teachings of the invention;

FIG. 2 is a plan view of an alternative embodiment of a prosthesis constructed in accordance with the teachings of the invention;

FIG. 3 is a side elevation view, taken along line 3—3 of FIG. 2;

FIG. 4 is a side elevation sectional view, taken along line 4—4 of FIG. 2;

FIG. 5 is a partially sectional side elevation view of an alternative embodiment of the prosthesis of the invention, similar to the view shown in FIG. 3;

FIG. 6 is a side elevation view of yet another embodiment of the invention, similar to the view of FIG. 3;

FIG. 7 is a side elevation, partially sectional view of a preferred embodiment of the invention, similar to the view of FIG. 6 but incorporating an arcuate, adjustable attachment structure;

FIG. 8 is a sectional view of the prosthesis of FIG. 7, illustrating flexure of the forefoot portion during, for example, ambulation, and further illustrating the adjustment means positioned in a forward position as compared to FIG. 7;

FIG. 9 is a side elevation, partially sectional view of a preferred embodiment of the invention, illustrating its utilization with a socket structure.

DESCRIPTION OF PREFERRED EMBODIMENT

Figure 10:
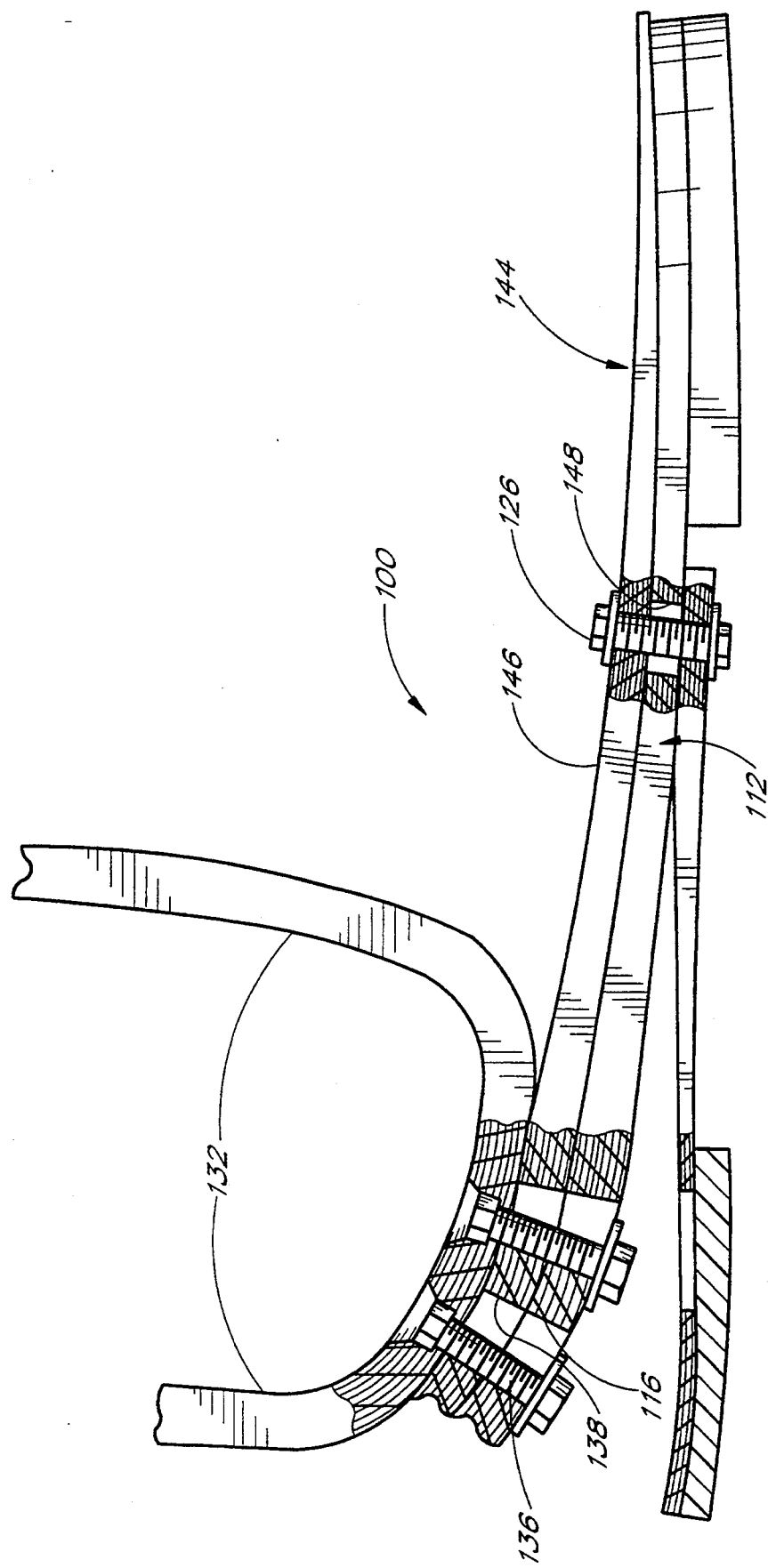
FIG. 10 is a side elevation, partially sectional view of another embodiment of the invention, illustrating the use of an auxiliary support or spring means.

The preferred embodiment of my invention is illustrated in FIGS. 7-9, as more fully described herein, but many of the basic fabrication techniques and principles of operation of my invention are similar for the embodiments set forth in FIGS. 1-5. Those fabrication techniques and principles of operation are described in some detail in my co-pending application, Ser. No. 07/585,920, and are briefly reviewed here.

Generally, the embodiments of FIGS. 1-5 include a foot prosthesis 10, FIG. 3, which includes a forefoot portion 12 and a heel portion 14 secured thereto. The forefoot portion 12 preferably includes an attachment section 22, a curvilinear ankle section 24, an arch section 26 and a toe section 28. The heel portion 14 preferably includes an attachment section 32 and a heel section 34 projecting rearwardly therefrom. The various sections of the forefoot and heel portions, respectively, are preferably formed integrally with one another and simultaneously by the incorporation of a plurality of laminae 16, FIG. 4, embedded in a hardened, flexible polymer, similar to the fabrication methods taught in my above-noted patents.

Although the ankle section 24 of the forefoot portion 12, as best shown in FIGS. 3-5, is configured to permit juxtaposition thereof to a rearward surface 66 and a lower surface 68 of a socket associated with the wearer's stump, the preferred embodiment of my instant invention, FIGS. 7-9, provides a prosthetic foot with an even lower profile, thereby making it more useable by persons with even lower amputations or providing an alternative to the configurations of FIGS. 1-5. Moreover, the embodiment of FIGS. 7-9 may be readily adapted for use in connection with a wide variety of other prosthetic devices such as, for example, being mounted on the lower end of a known prosthetic pylon tube (not shown).

Referring to the drawings, and particularly to FIG. 7 thereof, I show a foot prosthesis 100 constructed in accordance with the teachings of the invention and including a forefoot portion 112 and a heel portion 114 secured thereto.

The forefoot and heel portions of my invention, as well as the inventions of my above-noted patents, may be manufactured by any of a variety of expedients, including injection molding, resin-impregnation of laminates, the use of thermoplastic or thermoset materials and processes, or any of a range of combinations thereof.

Among other things, chopped fiber may be blended in a thermoplastic or thermoset resin and the resulting mixture injection molded into an appropriate configuration. Alternatively or additionally, thermoplastic laminae may be wound around an injection-molded core, or a thermoplastic resin may be injected between thermoplastic or thermoset laminae, whereby the laminates are bonded onto the injected material.

The forefoot portion 112 preferably includes an attachment section 116, and an arch section 118 and a toe section 120 extending forwardly thereof. In order to provide the desired energy transmission characteristics of my invention, these sections are preferably formed integrally and simultaneously with each other, and may include laminates extending through the entire length of the forefoot portion 112. The forefoot portion (as well as the heel portion 114) may be tapered or altered in cross-section along its length, in order to modify the energy-storage and release performance of the prosthesis. The fibers or laminates imbedded in the prosthesis may also be fayed or tapered to assist in or accomplish the same result.

The heel portion 114 preferably includes an attachment section 122 and a heel section 124 extending rearwardly therefrom. In the preferred embodiment, the heel portion 114 is demountably attached to the forefoot portion through the use of nut, washer and bolt combinations 126 or similar expedient, although permanent attachment of the heel through the use of epoxy, resin, or simultaneous forming may be utilized with efficacy. Demountable attachment is preferred, in that it permits the forefoot portion 112 to be selectably affixed to any of various heel portions 114 having different spring rates.

Pad members 128 may be affixed to the underside of the forefoot and heel portions, to create a profile for the bottom of the prosthesis 100 which corresponds to the interior of a shoe. Such a profile orients the foot 100, when the foot is in an unstressed state, at an appropriate angle for wearing shoes.

As illustrated in FIGS. 7 and 8, the preferred embodiment of my invention is utilized in connection with an attachment plate member 130. The plate member 130 preferably provides a curvilinear contact surface adjacent the attachment section 116, and is adapted to be incorporated into a socket 132, FIG. 9, or otherwise operatively attachable to a wearer's stump. The aforesaid incorporation into a socket 132 may be achieved through simultaneous formation of the socket 132 and the plate member 130, subsequent lamination or adhesion therebetween, or other expedient.

Further in the preferred embodiment, the attachment plate member 130 is operatively attached to the attachment section 116 through the provision of attachment and adjustment means 134 such as nut, washer and bolt combinations 136 or similar expedient. The adjustment means 134 further preferably includes mounting slots or holes 138 in the attachment section 116, which are elongated or otherwise of large enough dimension to permit the nut and bolt combinations 136 to be selectively positioned therein.

Those skilled in the art will understand that alternative embodiments of the invention include permanent affixation of the plate member 130 to the attachment section 116, or even direct formation or incorporation of the attachment section 116 into the socket 132. They will also understand, however, that the preferred embodiment of FIGS. 7-9 provides a beneficial adjustability and individual customization of the prosthetic foot which would not be achievable in such alternative constructions.

Specifically, the aforesaid selective positioning of the nut and bolt combinations 136 in the mounting slots or holes 138 permits rotating attitude adjustment and alignment of the prosthesis to accommodate an individual wearer's needs. The upper surface of the attachment section 116 may be radiused to correspond to the shape of the attachment plate 130 for this same purpose. In prototypes, this curvature has been utilized to permit an attitude adjustment of up to eight (8) degrees within a single prototype.

As shown in FIG. 8, the preferred assembly permits sliding movement of the plate 130 with respect to the attachment section 116, to and fro in the direction indicated by the arrow A. When a desired position is selected, the attachment means 134 may be appropriately tightened to provide frictional, non-sliding contact between the plate 130 and the attachment section 116.

The abovedescribed incorporation of the attachment plate member 130 into the socket 132, through lamination or otherwise, is preferably accomplished so that the justdescribed adjustability of the attachment means 134 is neither precluded nor interfered with. In short, the resulting socket 132 preferably has an outer profile which is configured to cooperate with its mating upper surface of the attachment section 116 in the manner described above.

The prosthesis of my invention further preferably includes cavity means 140 such as one or more cavities 142 correspondingly configured and positioned to receive any projecting portion of the adjustment means 134 during ambulation of said foot. Such ambulation and loaded condition of the prosthesis is illustrated in FIG. 8, showing the reception of the nut and bolt means 136 in the cavity 142. This cooperative relationship permits the attachment section 116 to be flexed downwardly, as shown by arrow B, FIG. 8, further than would be possible without the provision of the cavity 142. Such additional degree of flexure provides a corresponding additional degree of energy storage and release and improved performance of the prosthesis.

FIG. 6 illustrates an alternative embodiment of my invention. The heel portion 14 and the arch section 26 and toe section 28 of the forefoot portion 12 of FIG. 6 are also substantially the same as those illustrated in FIGS. 1-5. The embodiment of FIG. 6 differs from those of FIGS. 1-5, however, in that an attachment section 70, similar to attachment section 116 of FIGS. 7-9, is formed adjacent to and integrally with the arch section 26; the curvilinear ankle section 24 of FIG. 3 is not present in the embodiment of FIG. 6. Attachment means such as an attachment plate 72 and corresponding screws 74, FIG. 6, are provided adjacent the attachment section 70 to provide affixation to the wearer's socket, similar to socket 132 of FIG. 9.

The structure and method of this attachment may include, for example, any of those described in my co-pending application regarding attachment means 40 of FIGS. 1-4 or socket member 50 of FIG. 5. As indicated in FIG. 6, however, the front edge 76 of the attachment plate 72 is preferably provided with a curvilinear surface to reduce stress concentration in that area during flexure of the prosthesis.

As an alternative to the nut and bolt combinations 136 of FIGS. 7-9, in order to maximize the amount of flexure available with the prosthesis of FIG. 6, button-head screws 74 or other low-profile attachment means are preferred. As indicated above, higher profile attachment means have the disadvantage of contacting the heel section 34, FIG. 6, during heavy loading, thus preventing desired further flexure of the components of the prosthesis.

As indicated above, the forefoot and heel portions 112 and 114 are preferably fabricated from superimposed laminates such as laminates 16, FIG. 4, maintained in operative relationship by an encapsulating polymer and susceptible to bending stress determined by the thickness of the laminates. The preferred materials and fabrication process are more thoroughly described and explained in my abovementioned U.S. Pat. Nos. 4,547,913, 4,822,363, and 5,037,444 and include laminates such as carbon fibers and/or fiberglass or synthetic fibers such as Kevlar. Exemplary alternative methods and materials are described hereinabove.

The construction of the forefoot and heel portions 112 and 114 of my invention thus preferably includes continuous, integrally and simultaneously formed sections 116, 118, and 120, and 122 and 124, respectively. The aforesaid sections are fabricated as unitary structures by polymer impregnation of the aforedescribed superimposed reinforcing laminae. As a result of the materials, design and construction of the prosthetic foot 10, the various sections are capable of spring stress generated energy storage whereby the subjection of the prosthetic foot of my invention to bending moments or other stress loading will cause transmission of spring stress through said sections.

It will be obvious to those skilled in the art that a virtually infinite variety of forefoot portions 112 and heel portions 114 may be fabricated, each having unique spring stress response characteristics determined by the configuration, composition and amount of the various component materials utilized therein. The aforementioned demountable connection of the heel portion to the forefoot portion therefore permits interchangeability of those portions to match the weight, stride and activity schedule of the wearer utilizing the prosthetic foot.

The foot 100 may be affixed to the wearer by any of several means. As described above, a socket 132 may be affixed directly to the foot 100. Alternatively, a tubular pylon (not shown) may be attached to the foot through the use of epoxy, glue, brackets or the like. For amputees who may utilize tubular pylons, however, a greater degree of energy storage and release may be provided by certain of my other aforementioned inventions.

The attachment section 116, when assembled with the attachment means 134, is substantially rigid and capable of sustaining torsional, impact, and other loads impressed thereupon by the wearer during use of the foot 100. In addition, the inherent rigidity of the attachment section prevents it from being distorted in any way and causes the effective transmission of the aforesaid loads imposed thereupon between the wearer and the prosthetic foot 100.

A cosmetic shroud similar to the shroud 64, FIG. 5, may be utilized to encapsulate the foot 10, in a manner more fully explained in my previously-described patents.

In addition to the foregoing, those skilled in the art will understand that auxiliary support or spring means 144 such as flexure members 146, FIG. 10, may be efficaciously utilized in connection with any embodiment of the abovedescribed invention, without departing from the scope of the teachings hereof. Although a broad variety of auxiliary spring means 144 may be utilized with efficacy, including a range of configurations and sizes and locations on the prosthesis 100, the embodiment of FIG. 10 is illustrative.

In FIG. 10, the auxiliary support member 146 is configured similarly to the forefoot portion 112. Nut and bolt combinations 126 and 136, or similar expedient, are utilized to retain the various components in operative alignment. In order to permit the desired flexure of each of members 112 and 146 independently from each other, an oversized opening such as opening 148 is preferably provided in either or both of members 112 and 146. This ensures that, if the members are fixed with respect to each other at a location, for example, such as the attachment section 116, the remainder of the members 112 and 146 may slide with respect to each other when deformation of the prosthesis occurs (during ambulation or the like).

As indicated above, those skilled in the art will understand that the auxiliary support members may be provided by a wide variety of configurations, positioned to cooperatively function with the rest of the prosthesis 100. Such auxiliary support members may be attached at various locations and in various manners on the prosthesis 100 without departing from the scope of the invention.

Among other things, these auxiliary support members permit the energy-storage and -release characteristics of the foot 100 to be refined and fine-tuned. In that regard, the auxiliary support members 146 are preferably constructed from materials, and fabricated by techniques, similar to those from which and by which the other components of the foot 100 are constructed and fabricated.

An important aspect of the polymers and laminates referred to hereinabove is that they are characterized by needed, but not excessive, flexural deflection under load, which characteristic permits the shock-absorption stress loading of the prosthesis 100 while maintaining sufficient stability to prevent the collapse of the prosthesis while loads are imposed thereupon.

To achieve the relatively thin construction of the forefoot and heel portions 12 and 14, the aforesaid polymers are preferably utilized in conjunction with various fibers and/or laminating materials.

There is a wide variety of fibrous reinforcements available at the present time, including such inorganic fibers as glass or carbon fibers.

The prosthetic foot of my invention can thus be provided in different sizes to correspond to the size of the natural foot of the wearer of the prosthesis 100. When such different sizes are provided, corresponding reduction or increase in the cross-section and/or the number of laminae and thickness of taper, if any, of the respective sections of the forefoot and heel portions 112 and 114 can be made to provide for the proper flexure of said sections.

Moreover, and as mentioned above, the flexibility of the prosthetic foot of my invention may be further increased, while still maintaining acceptable strength characteristics, by providing an auxiliary support member or auxiliary forefoot portion such as auxiliary means 144, FIG. 10. Such an auxiliary member or portion is preferably operatively positioned with respect to the forefoot portion 112 to provide the desired support while permitting some relative movement therebetween, thereby permitting the desired flexure.

By such a construction, the same total thickness of supportive material is achieved in an assembly of overlying, juxtaposed, thin layers, which construction has much more flexibility than does a unitary forefoot portion of the same total material thickness. Such an auxiliary support member can be especially beneficial in the construction of FIG. 6–9.

The aforementioned flexure of the foot portions 112 and 114 provides the capacity for increased surface area contact between the bottom surfaces of the foot 100 and the adjacent surface, during both the energy impact and delivery phases of the prosthesis 100. It will be noted that the elongated structure of the portions 112 and 114, together with their aforesaid flexure capabilities, provides for a relatively extended lever arm which achieves stress storage and stress reaction.

The preferred method of manufacturing the forefoot and heel portions 112 and 114 of the prosthesis 100 is by a thermosetting molding process including the utilization of molds having properly shaped and sized cavities. The cavities are designed to receive the requisite number of laminates or fibers and the proper volume of polymer, such that the portions 12 and 14 are respectively unitary structures, with the various sections thereof formed simultaneously within each respective portion.

Unlike prior art unitary devices, the fitting of the prosthesis 100 involves the judicious adjustment of the prosthesis by the proper combination of forefoot and heel portions 112 and 114. Only when the proper correlation has been accomplished, can the cosmetic shroud be installed upon the assembled, respective portions of the prosthesis 100.

By the prosthesis of my invention I provide a foot prosthesis which can be carefully matched to the weight, stride and physical characteristics of the wearer. This is accomplished by carefully balancing the respective physical characteristics of the forefoot and heel portions 112 and 114 and the various sections thereof.

Moreover, the assembled prosthesis is far lighter in weight than prior art prostheses since the inherent design and structure of the prosthesis, the materials used and the careful calculation of stress factors of the components of the prosthesis permit fine-tuning of the prosthesis to the needs of the wearer thereof.

The prosthesis of my invention has been described with some particularity but the specific designs and constructions disclosed are not to be taken as delimiting of the invention in that various obvious modifications will at once make themselves apparent to those of ordinary skill in the art, all of which will not depart from the essence of the invention and all such changes and modifications are intended to be encompassed within the appended claims.

I claim:

1. A low profile Symes foot prothesis for an amputee who has undergone a Symes amputation in which the amputee's foot is severed from the amputee's leg near the amputee's ankle region, said foot prosthesis being adapted to be secured to a socket positioned on said amputee's ankle region, said foot prosthesis comprising:

a connecting member adapted to be operatively mounted to said socket positioned on the ankle region of said amputee, said connecting member having a lower surface having first curvature thereon;

a generally horizontally oriented flexible prosthetic foot member adjustably secured to said connecting member, said foot member being capable of storing and releasing energy during utilization of said foot prosthesis, said foot member comprising:

a generally planar upper auxiliary section for adjustably mounting onto the underside of said connecting member, said auxiliary section having an upper attachment surface having a second curvature, the degree of which is less than the degree of said first curvature of said connecting member, wherein the difference in the degree of said first and second curvatures permits said auxiliary section to flex relative to said connecting member without said connecting member causing stress concentrations on said auxiliary section during utilization of said foot member, said upper attachment surface being located proximate the rearward end of said foot member for mounting onto said connecting member, said auxiliary section extending forwardly therefrom to form a forward lever arm, and being capable of providing energy storage and release characteristics during utilization of said foot prosthesis;

a generally planar intermediate section for adjustably mounting onto the underside of said auxiliary section, said intermediate section having a second upper attachment surface located proximate the rearward end of said foot member, wherein said intermediate section extends relatively forward therefrom to a toe section and has a forwardly extending lever arm which provides energy storage and release characteristics during utilization of said prothesis, wherein a the forward extending end of said auxiliary section slides relative to a forward extending portion of said intermediate section during utilization of said foot prosthesis, said auxiliary section helping to resist the upper deflection of said intermediate section; and a generally planar heel section adjustably mounted onto the underside of said intermediate section proximate a middle portion of said intermediate section, said heel section extending relatively rearward therefrom to form a rearwardly extending leaf spring lever arm that flexes relative to said intermediate section.

2. The foot prosthesis of claim 1, wherein said sections of said foot member are substantially planar and have a substantially low profile.

3. The foot prosthesis of claim 1, wherein said connecting member and said foot member are secured together by at least one nut and bolt member.

4. The foot prosthesis of claim 3, wherein said nut and bolt member extends from said connecting member and through an aperture in said auxiliary section and said intermediate section, said apertures being slightly larger than said bolt member to permit translatory movement of said connecting member relative to said auxiliary and intermediate sections.

5. The foot prosthesis of claim 1, wherein by adjusting the translatory position of said connecting member relative to said upper attachment surface, the angular position of said connecting member relative to said foot member can be adjusted, the degree of said angular adjustment being dependent on the degree of said second curvature and the translatory location of said connecting member relative to said upper attachment surface.

6. The foot prosthesis of claim 1, wherein said heel section is adjustably and demountably secured to said intermediate section by at least one nut and bolt member.

7. A low profile Symes foot prothesis for an amputee who has undergone a Symes amputation in which the amputee's foot is severed from the leg near the amputee's ankle region, said foot prosthesis being adapted to be secured to a socket positioned on said amputee's ankle region, said foot prosthesis comprising:

an upper connecting member adapted to be operatively mounted to said socket postioned on said ankle region of said amputee, said upper connecting member being slightly curved in order to accommodate the shape of said socket;

a generally horizontally oriented and substantially planar flexible foot member, said foot member being substantially low in profile so as to fit underneath said ankle region of said amputee and extending generally forwardly from the underside of said connecting member to form a forward lever arm, said foot member being capable of storing and releasing energy, and comprising:

an attachment section located proximate the rearward end of said foot member, wherein said attachment section is adjustable relative to said connecting member and has an upper attachment surface adapted to be operatively mounted onto said connecting member, said upper attachment surface having an upper surface extending generally along a slightly curved plane, wherein the position of said upper connecting member relative to said attachment section can be adjusted to determine both the vertical and horizontal angles at which said connecting member is positioned relative to said foot member, said angles being adjustable by sliding said connecting member in a translatory manner relative to said slightly curved plane; and a forefoot section extending from said attachment section, said forefoot section extending along the same slightly curved plane as said attachment section to a forward extending toe section, said toe section forming a forward lever arm for said foot prosthesis;

a generally planar heel member extending rearward from the underside of said foot member to provide a rearward lever arm for said foot member.

8. The foot prosthesis of claim 7, wherein said upper connecting member is secured to said attachment section proximate the rearward end of said foot member, enabling said foot member to have an extended forward lever arm.

9. The foot prosthesis of claim 7, wherein said foot member is removable from said connecting member and said heel member is removable from said foot member, said members being replaceable such that various size members can be utilized to adjust the flex characteristics of said foot prosthesis.

10. The foot prosthesis of claim 7, wherein said foot member is secured to said connecting member by at least one nut and bolt member, said nut and bolt member extending through an aperture in said foot member, said aperture being slightly larger than said bolt member to permit said connecting member to slide relative to said foot member.

11. The foot prosthesis of claim 7, wherein the bottom surface of said connecting member has a first curvature and said attachment section of said foot member has a second curvature, wherein the difference in said curvatures helps reduce the stress concentrations imposed on said foot member during flexure of said foot prosthesis.

12. The foot prosthesis of claim 7, wherein said attachment section comprises an auxiliary spring extending forwardly from said connecting member, said auxiliary spring storing and releasing energy and deflecting upward as said forefoot section deflects upward.

13. The foot prosthesis of claim 7, wherein said heel member is secured at its forward end to the underside of said foot member and said heel member extends rearward therefrom, said heel member being adapted to flex relative to said foot member during utilization of said foot prothesis, said heel member having a recess therein for receiving a downwardly extending end of a nut and bolt member extending downwardly from said attachment section of said foot member such that during flexing of said foot prosthesis, said downwardly extending end of said nut and bolt member does not contact or damage said heel member, and said heel member is free to flex.

14. The foot prosthesis of claim 7, wherein said upper connecting member can be adjusted angularly and vertically up to about 8° relative to said foot member by adjusting the translatory position of said upper connecting member relative to said attachment section.

15. The foot prothesis of claim 7, wherein the position of said upper connecting member relative to said foot member can be adjusted such that the horizontal angle at which said foot member is positioned relative to said upper connecting member can be adjusted so that said foot member can be positioned with the toe in or toe out.

16. The foot prothesis of claim 7, wherein the flexibility characteristics of said foot member are determined by the thickness of said foot member.

* * * * *

UNITED STATES PATENT AND TRADEMARK OFFICE
CERTIFICATE OF CORRECTION

PATENT NO.  : 5,376,141
DATED       : December 27, 1994
INVENTOR(S) : Van L. Phillips It is certified that error appears in the above-indentified patent and that said Letters Patent is hereby corrected as shown below:

Column 10, Line 22:  insert --a-- after "a lower surface having "

Column 10, Line 57:  delete --the--

Signed and Sealed this

Seventh Day of March, 1995

Attest:

BRUCE LEHMAN

Attesting Officer     Commissioner of Patents and Trademarks